US012753135B2

(12) United States Patent
Takakuwa et al.

(10) Patent No.: US 12,753,135 B2
(45) Date of Patent: Oct. 6, 2026

(54) METHOD FOR PRODUCING REACTION GAS CONTAINING 1,1,2-TRIFLUOROETHANE (R-143) AND/OR (E,Z)-1,2-DIFLUOROETHYLENE (R-1132(E,Z))

(71) Applicant: DAIKIN INDUSTRIES, LTD., Osaka (JP)

(72) Inventors: Tatsuya Takakuwa, Osaka (JP); Tomo Otsuka, Osaka (JP); Atsushi Noguchi, Osaka (JP); Yuuta Hasumoto, Osaka (JP)

(73) Assignee: DAIKIN INDUSTRIES, LTD., Osaka (JP)

( * ) Notice: Subject to any disclaimer, the term of this patent is extended or adjusted under 35 U.S.C. 154(b) by 572 days.

(21) Appl. No.: 18/209,652

(22) Filed: Jun. 14, 2023

(65) Prior Publication Data

US 2023/0391696 A1 Dec. 7, 2023

Related U.S. Application Data

(63) Continuation of application No. PCT/JP2021/046641, filed on Dec. 16, 2021.

(30) Foreign Application Priority Data

Dec. 16, 2020 (JP) ............................ JP2020-208846

(51) Int. Cl.
*C07C 17/269* (2006.01)

(52) U.S. Cl.
CPC .................................. *C07C 17/269* (2013.01)

(58) Field of Classification Search
CPC ............................ C07C 17/269; C07C 17/281
See application file for complete search history.

(56) References Cited

U.S. PATENT DOCUMENTS

| | | | |
|---|---|---|---|
| 5,059,729 | A | 10/1991 | Gervasutti |
| 2021/0130268 | A1 | 5/2021 | Takakuwa et al. |
| 2021/0163381 | A1 | 6/2021 | Komatsu |

FOREIGN PATENT DOCUMENTS

| | | |
|---|---|---|
| JP | 1-287044 | 11/1989 |
| JP | 2013-241348 | 12/2013 |

(Continued)

OTHER PUBLICATIONS

Machine translation of WO2020246611, Dec. 10, 2020, pp. 1-39 (Year: 2020).*

(Continued)

*Primary Examiner* — Medhanit W Bahta
(74) *Attorney, Agent, or Firm* — Wenderoth, Lind & Ponack, L.L.P.

(57) ABSTRACT

The present disclosure provides a method for producing a reaction gas containing 1,1,2-trifluoroethane (R-143) and/or (E,Z)-1,2-difluoroethylene (R-1132(E,Z)) using a starting material that is easier to obtain than those used in conventional methods. Specifically, the present disclosure provides a method for producing a reaction gas containing 1,1,2-trifluoroethane (R-143) and/or (E,Z)-1,2-difluoroethylene (R-1132(E,Z)), the method comprising subjecting a starting material gas containing difluoromethane (R-32) to a reaction that involves thermal decomposition at a pressure of 0.6 MPaG or more and 2.0 MPaG or less and a temperature of 600° C. or more and 1000° C. or less, thereby obtaining the reaction gas.

10 Claims, 1 Drawing Sheet

(56) References Cited

FOREIGN PATENT DOCUMENTS

| | | | |
|---|---|---|---|
| WO | 2017/104828 | 6/2017 | |
| WO | WO-2019194214 A1 * | 10/2019 | ............ C07C 17/25 |
| WO | 2019/216239 | 11/2019 | |
| WO | 2020/246611 | 12/2020 | |

OTHER PUBLICATIONS

Machine translation of WO2019194214A1, Oct. 10, 2019, pp. 1-17 (Year: 2019).*
Machine translation of JP2013241348A, Dec. 5, 2013, pp. 1-21 (Year: 2013).*
International Search Report issued Feb. 22, 2022 in International (PCT) Application No. PCT/JP2021/046641.
International Preliminary Report on Patentability issued Jun. 13, 2023 in International (PCT) Application No. PCT/JP2021/046641, with English-language translation.
Extended European Search Report dated Oct. 24, 2024 in corresponding European Patent Application No. 21906709.7.

* cited by examiner

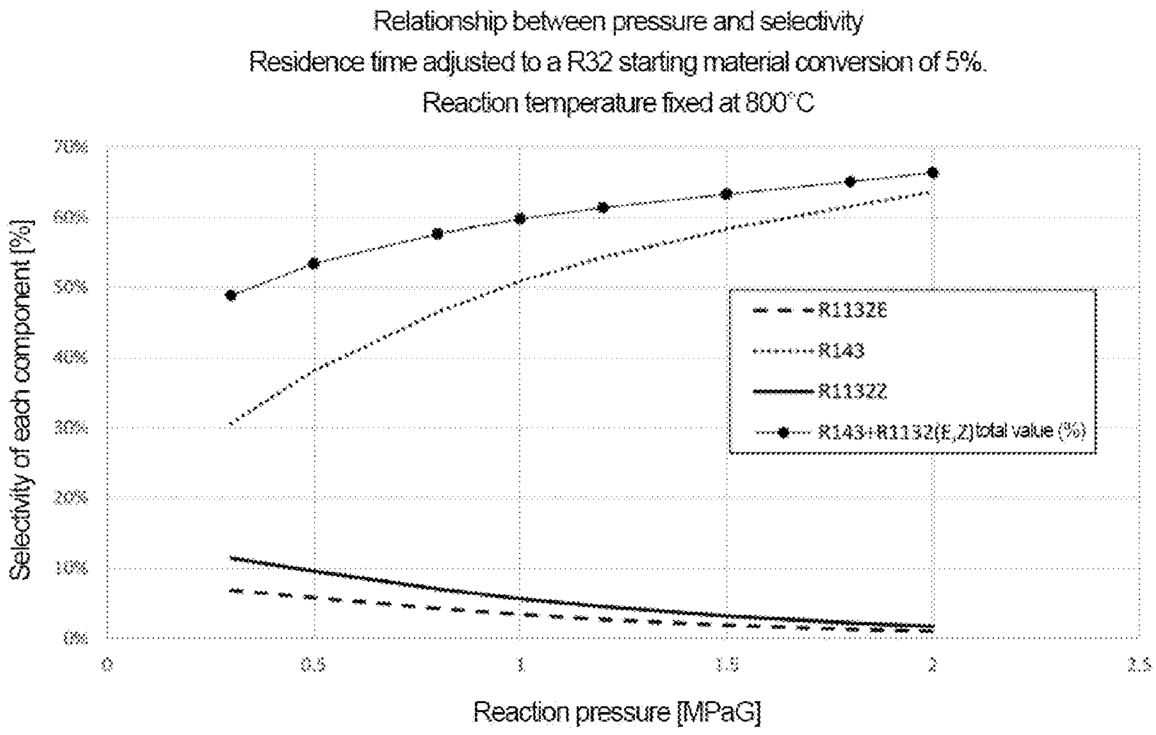
Relationship between pressure and selectivity
Residence time adjusted to a R32 starting material conversion of 5%.
Reaction temperature fixed at 800°C
Selectivity of each component [%]
70%
60%
50%
40%
30%
20%
10%
0%
0
0.5
1
1.5
2
2.5
Reaction pressure [MPaG]
R1132E
R143
R1132Z
R143+R1132(E,Z) total value (%)

METHOD FOR PRODUCING REACTION GAS CONTAINING 1,1,2-TRIFLUOROETHANE (R-143) AND/OR (E,Z)-1,2-DIFLUOROETHYLENE (R-1132(E,Z))

TECHNICAL FIELD

The present disclosure relates to a reaction gas containing 1,1,2-trifluoroethane (R-143) and/or (E,Z)-1,2-difluoroethylene (R-1132(E,Z)).

BACKGROUND ART 1,1,2-trifluoroethane (R-143) is known as an intermediate for synthesizing (E,Z)-1,2-difluoroethylene (also referred to below as "R-1132(E,Z)") by subjecting it to a dehydrofluorination reaction. (E)-1,2-Difluoroethylene (also referred to below as "R-1132(E)"), which has a low global warming potential (GWP), is attracting attention as an alternative refrigerant for difluoromethane (R-32) or 1,1,1,2,2-pentafluoroethane (R-125), which are greenhouse gases.

PTL 1 discloses a method for producing 1,2-difluoroethane and 1,1,2-trifluoroethane, and discloses, on page 3, upper left column, a method for selectively producing 1,1,2-trifluoroethane, comprising reacting 1-chlorotrifluoroethylene (CTFE) with hydrogen in the presence of a hydrogenation catalyst in the gas phase at a temperature ranging from 100 to 220° C.

CITATION LIST

Patent Literature

PTL 1: JPH01-287044A

SUMMARY

A method for producing a reaction gas containing 1,1,2-trifluoroethane (R-143) and/or (E,Z)-1,2-difluoroethylene (R-1132(E,Z)), the method comprising subjecting a starting material gas containing difluoromethane (R-32) to a reaction that involves thermal decomposition at a pressure of 0.6 MPaG or more and 2.0 MPaG or less and a temperature of 600° C. or more and 1000° C. or less, thereby obtaining the reaction gas.

Advantageous Effects

The method for producing a reaction gas containing 1,1,2-trifluoroethane (R-143) and/or (E,Z)-1,2-difluoroethylene (R-1132(E,Z)) according to the present disclosure is capable of producing the reaction gas using a starting material that is easier to obtain than those used in conventional methods.

BRIEF DESCRIPTION OF THE DRAWING

The FIGURE is a graph demonstrating the effect of difference in reaction pressure on the reaction results of Experimental Example 5.

DESCRIPTION OF EMBODIMENTS

The method for producing a reaction gas containing 1,1,2-trifluoroethane (also referred to as "R-143") and/or (E,Z)-1,2-difluoroethylene (also referred to as "R-1132(E,Z)") according to the present disclosure is described in detail below. (E,Z)-1,2-difluoroethylene (R-1132(E,Z)) refers to E-1,2-difluoroethylene (R-1132(E)) and/or Z-1,2-difluoroethylene (R-1132(Z)).

In the present specification, the term "pre-pressurization" means that a starting material gas is pressurized to a predetermined pressure in advance outside the reactor before being supplied to the reactor.

In the present specification, the term "preheating" means that a starting material gas, a heat medium, an additive gas, and the like are heated to a predetermined temperature in advance (so-called preheated) outside the reactor before being supplied to the reactor.

In the present specification, the term "conversion" refers to the ratio (mol %) of the total molar concentration of compounds other than difluoromethane (also referred to as "R-32") contained in the gas (=reaction gas) flowing out of the reactor outlet to the molar concentration of R-32 supplied to the reactor.

In the present specification, the term "selectivity" refers to the ratio (mol %) of the molar concentration of the target compound (e.g., R-143) contained in the gas (=reaction gas) flowing out of the reactor outlet to the total molar concentration of compounds other than R-32 contained in the gas.

In the present specification, a numerical range indicated by " . . . to . . . " means a range including the numerical values before and after "to" as the lower limit and the upper limit.

The method for producing a reaction gas containing 1,1,2-trifluoroethane (R-143) and/or (E,Z)-1,2-difluoroethylene (R-1132(E,Z)) according to the present disclosure comprises subjecting a starting material gas containing difluoromethane (R-32) to a reaction that involves thermal decomposition (synthesis reaction accompanying thermal decomposition of R32) under specific conditions, thereby obtaining the reaction gas. More specifically, the method can be roughly divided into the following embodiments 1 to 4.

Embodiment 1

A method for producing a reaction gas containing 1,1,2-trifluoroethane (R-143) and/or (E,Z)-1,2-difluoroethylene (R-1132(E,Z)), the method comprising subjecting a starting material gas containing difluoromethane (R-32) to a reaction that involves thermal decomposition at a pressure of 0.6 MPaG or more and 2.0 MPaG or less and a temperature of 600° C. or more and 1000° C. or less, thereby obtaining the reaction gas.

Embodiment 2

A method for producing a reaction gas containing 1,1,2-trifluoroethane (R-143) and/or (E,Z)-1,2-difluoroethylene (R-1132(E,Z)), the method comprising supplying a starting material gas containing difluoromethane (R-32), which has been pre-pressurized to a pressure of 0.1 MPaG or more and 2.0 MPaG or less, in a reactor under a pressure condition lower than the pre-pressurization pressure, and subjecting the starting material gas to a reaction that involves thermal decomposition at a temperature of 600° C. or more and 1000° C. or less, thereby obtaining the reaction gas.

Embodiment 3

A method for producing a reaction gas containing 1,1,2-trifluoroethane (R-143) and/or (E,Z)-1,2-difluoroethylene (R-1132(E,Z)), the method comprising supplying a starting material gas containing difluoromethane (R-32) and a heat medium with a temperature of 600° C. or more and 1000° C. or less in a reactor, and subjecting the starting material gas to a reaction that involves thermal decomposition at a temperature of 600° C. or more and 1000° C. or less, thereby obtaining the reaction gas.

Embodiment 4

A method for producing a reaction gas containing 1,1,2-trifluoroethane (R-143) and/or (E,Z)-1,2-difluoroethylene (R-1132(E,Z)), the method comprising, before supplying a starting material gas containing difluoromethane (R-32) in a reactor, combining the starting material gas with a hydrofluorocarbon gas and/or a hydrochlorofluorocarbon gas in an amount of 10% or less of the volume of the difluoromethane (R-32) to form a mixed gas, and subjecting the mixed gas to a reaction that involves thermal decomposition at a temperature of 600° C. or more and 1000° C. or less, thereby obtaining the reaction gas.

According to the methods for producing a reaction gas containing 1,1,2-trifluoroethane (R-143) and/or (E,Z)-1,2-difluoroethylene (R-1132(E,Z)) of the present disclosure having the above features, the reaction gas can be produced by using a starting material that is easier to obtain than those used in conventional methods. Although it is difficult to obtain CTFE, which is a starting material of conventional methods, it is easy to obtain the starting material gas containing difluoromethane (R-32) used in the present disclosure.

The present application also includes a method for producing (E,Z)-1,2-difluoroethylene (R-1132(E,Z)), wherein in the production method according to any one of embodiments 1 to 4 above, when the reaction gas contains 1,1,2-trifluoroethane (R-143), the method comprises subjecting 1,1,2-trifluoroethane (R-143) contained in the reaction gas to a dehydrofluorination reaction.

Embodiments 1 to 4 are described below.

Embodiment 1

Embodiment 1 is a method for producing a reaction gas containing R-143 and/or R-1132(E,Z), the method comprising subjecting a starting material gas containing R-32 to a reaction that involves thermal decomposition at a pressure of 0.6 MPaG or more and 2.0 MPaG or less and a temperature of 600° C. or more and 1000° C. or less, thereby obtaining the reaction gas.

In embodiment 1, the starting material gas containing R-32 is subjected to a reaction that involves thermal decomposition (also simply referred to below as “the reaction”) at a pressure of 0.6 MPaG or more and 2.0 MPaG or less and a temperature of 600° C. or more and 1000° C. or less, whereby a reaction gas containing R-143 and/or R-1132(E,Z), which are the target compounds, can be synthesized. The operation of pressurizing the starting material gas to a predetermined pressure and the operation of subjecting the starting material gas to the reaction at a predetermined temperature can be performed inside a reactor.

In embodiment 1, R-32 alone may be directly supplied to a reactor as the starting material gas, or R-32 may be supplied after being diluted with an inert gas, such as nitrogen, argon, or carbon dioxide. The content of R-32 in the starting material gas is not limited, but is preferably adjusted in the range of 10 volume % or more and 100 volume % or less, and more preferably 90 volume % or more and 100 volume % or less. By diluting the starting material gas to this range, it is easy to obtain an effect of suppressing a side reaction (caulking) in which R-32 is completely dehydrofluorinated to generate carbon.

The pressure (reaction pressure) at which the starting material gas is subjected to the reaction may be 0.6 MPaG or more and 2.0 MPaG or less, and in this range, preferably 1.2 MPaG or more and 2.0 MPaG or less, and more preferably 1.5 MPaG or more and 2.0 MPaG or less. When the pressure is set within this range, both the conversion of R-32 and the selectivity of R-143 and/or R-1132(E,Z) can be improved.

The starting material gas is preferably pre-pressurized to a pressure exceeding the reaction pressure before being supplied to the reactor. The pressure condition of pre-pressurization can be appropriately selected from a pressure range exceeding 0.6 MPaG (e.g., more than 0.6 MPaG and 2.1 MPaG or less). Pre-pressurization can be performed using a known compressor or the like. The lower limit of the pressure condition of pre-pressurization can be set to 0.7 MPaG or more, 0.8 MPaG or more, or the like.

The temperature (reaction temperature) at which the starting material gas is subjected to the reaction may be 600° C. or more and 1000° C. or less, and in this range, preferably 700° C. or more and 900° C. or less, and more preferably 800° C. or more and 850° C. or less. When the reaction temperature is set within this range, both the conversion of R-32 and the selectivity of R-143 and/or R-1132(E,Z) can be improved.

The heating method used when subjecting the starting material gas to the reaction may be a known method. Examples include a method of heating a reactor (reaction container) in an electric furnace, a method of heating a reactor with an electric heater or a jacket through which a heat medium is circulated, a method of heating a reactor in a microwave oven, a method in which the inert gas as a diluent gas is heated and then mixed with R-32, and any combination of these methods.

The time (residence time) for subjecting the starting material gas to the reaction is in accordance with the reaction temperature, reaction pressure, and the like, and cannot be unconditionally determined. However, it is preferably 0.01 seconds or more and 10 seconds or less, and more preferably 0.10 seconds or more and 1 second or less. When the residence time is set to a value equal to or more than the lower limit of the above range, the thermal decomposition of R-32 is promoted, and R-143 and/or R-1132(E,Z) can be obtained efficiently. Further, when the residence time is set to a value equal to or less than the upper limit of the above range, side reactions are suppressed, and the thermal decomposition of R-32 is promoted, improving the productivity.

The form of the reactor in which the starting material gas is subjected to the reaction is not limited, and known reactors capable of withstanding the reaction temperature and reaction pressure stated above are widely usable. For example, a tubular flow reactor packed with a catalyst may be used. Examples of the catalyst include metal oxide catalysts, such as $Al_2O_3$ and $CoO_2$; metal catalysts, such as Fe, Zn, and Co; and catalysts in which metal particles are supported on oxide or carbon carriers, such as Pd/C and $Pd/TiO_2$. When the reaction is performed in the absence of a catalyst, the reactor may be, for example, a hollow adiabatic reactor, or an adiabatic reactor packed with a porous or non-porous metal or medium that improves the mixing state of the starting material gas. Also usable is a multitubular reactor or the like in which a heat medium is used to cool the reactor and/or to homogenize the temperature distribution within the reactor.

When a hollow reactor is used, in a method wherein a reactor with a smaller inner diameter is used to improve heat transfer efficiency, it is preferable, for example, that the relationship between the flow rate of the starting material gas and the inner diameter of the reactor be adjusted so that a high linear velocity and a large heat transfer area are obtained.

Specifically, the reactor is preferably formed of a material that is resistant to the corrosive action, such as Hastelloy, Inconel, Monel, Incoloy, and stainless steel materials (e.g., SUS316). When a metal reactor with an iron content of 10 mass % or less, such as a reactor of Hastelloy or Inconel, is used from among the reactors above, the occurrence of caulking on the reactor inner wall can also be suppressed.

The reaction gas containing R-143 and/or R-1132(E,Z) obtained in embodiment 1 may be appropriately subjected to a purification step to extract high-purity R-143 and/or R-1132 (E,Z). The purification method may be a known purification method, such as distillation. In embodiment 1, although it depends on the reaction conditions, in a preferred embodiment, the selectivity of R-143 is 20 mol % or more (particularly 30 to 60 mol %), the selectivity of R-1132(E) is 2 mol % or more (particularly 2 to 7 mol %), the selectivity of R-1132(Z) is 3 mol % or more (particularly 3 to 11 mol %), and the total selectivity of these is preferably 25 mol % or more (particularly 30 to 70 mol %).

When the reaction gas of embodiment 1 contains R-143, R-143 contained in the reaction gas is used as a new starting material gas, and R-143 is dehydrofluorinated, whereby a reaction gas containing R-1132(E,Z) can be obtained. Although R-1132(E,Z) can be directly synthesized by subjecting a starting material gas containing R-32 to a reaction that involves thermal decomposition (synthesis of R-1132 (E,Z) by reaction between CHF carbenes (CHF·) obtained by dehydrofluorination of R-32), there is a characteristic that the amount of by-products is smaller when R-1132(E,Z) is obtained by once obtaining a reaction gas containing R-143 through embodiment 1, using R-143 as a new starting material gas, and dehydrofluorinating R-143. That is, R-143 contained in the reaction gas of embodiment 1 is useful as a new starting material gas for obtaining R-1132(E,Z) with high selectivity.

Embodiment 2

Embodiment 2 is a method for producing a reaction gas containing R-143 and/or R-1132(E,Z), the method comprising supplying a starting material gas containing difluoromethane (R-32), which has been pre-pressurized to a pressure of 0.1 MPaG or more and 2.0 MPaG or less, in a reactor under a pressure condition lower than the pre-pressurization pressure, and subjecting the starting material gas to a reaction that involves thermal decomposition at a temperature of 600° C. or more and 1000° C. or less, thereby obtaining the reaction gas.

In embodiment 2, a starting material gas containing difluoromethane (R-32), which has been pre-pressurized to a pressure of 0.1 MPaG or more and 2.0 MPaG or less, is supplied to a reactor under a pressure condition lower than the pre-pressurization pressure, and subjected to a reaction that involves thermal decomposition (also simply referred to below as "the reaction") at a temperature of 600° C. or more and 1000° C. or less, whereby a reaction gas containing R-143 and/or R-1132(E,Z), which are the target compounds, can be synthesized. The operation of pre-pressurizing the starting material gas to a predetermined pressure can be performed using a known compressor or the like before supplying it to the reactor, and the operation of subjecting the starting material gas to the reaction at a predetermined pressure and a predetermined temperature can be performed inside the reactor. Further, the starting material gas can be preheated simultaneously with or separately from pre-pressurization, if necessary. The lower limit of pre-pressurization is 0.5 MPaG or more (or more than 0.5 MPaG), 1.0 MPaG or more (or more than 1.0 MPaG), 1.5 MPaG or more (or more than 1.5 MPaG), or the like.

In embodiment 2, R-32 alone may be directly supplied to a reactor as the starting material gas, or R-32 may be supplied after being diluted with an inert gas, such as nitrogen, argon, or carbon dioxide. The content of R-32 in the starting material gas is not limited, but is preferably adjusted in the range of 10 volume % or more and 100 volume % or less, and more preferably 90 volume % or more and 100 volume % or less. By diluting the starting material gas to this range, it is easy to obtain an effect of suppressing a side reaction (caulking) in which R-32 is completely dehydrofluorinated to generate carbon.

The pressure (reaction pressure) at which the starting material gas is subjected to the reaction may be in the range of 0 MPaG or more and less than 2.0 MPaG (or 1.9 MPa or less) and lower than the pre-pressurization pressure. In this range, the reaction pressure is preferably 1.2 MPaG or more and less than 2.0 MPaG (or 1.9 MPa or less), and more preferably 1.5 MPaG or more and less than 2.0 MPaG (or 1.9 MPa or less). When the pressure is set within this range, both the conversion of R-32 and the selectivity of R-143 and/or R-1132(E,Z) can be improved.

In embodiment 2, by setting the reaction pressure of the starting material gas to a pressure condition lower than the pre-pressurization pressure, the starting material gas is easily supplied to the reactor, and a portion where the concentration of R-32 is locally high is generated in the starting material gas supplied to the reactor. As a result, CHF carbenes (CHF·) generated by the decomposition of R-32 are easily reacted with R-32, and R-143 is easily obtained.

The temperature (reaction temperature) at which the starting material gas is subjected to the reaction may be 600° C. or more and 1000° C. or less, and in this range, preferably 700° C. or more and 900° C. or less, and more preferably 800° C. or more and 850° C. or less. When the reaction temperature is set within this range, both the conversion of R-32 and the selectivity of R-143 and/or R-1132(E,Z) can be improved.

The heating method used when subjecting the starting material gas to the reaction may be a known method. Examples include a method of heating a reactor (reaction container) in an electric furnace, a method of heating a reactor with an electric heater or a jacket through which a heat medium is circulated, a method of heating a reactor in a microwave oven, a method in which the inert gas as a diluent gas is heated and then mixed with R-32, and any combination of these methods.

The time (residence time) for subjecting the starting material gas to the reaction is in accordance with the reaction temperature, reaction pressure, and the like, and cannot be unconditionally determined. However, it is preferably 0.01 seconds or more and 10 seconds or less, and more preferably 0.10 seconds or more and 1 second or less. When the residence time is set to a value equal to or more than the lower limit of the above range, the thermal decomposition of R-32 is promoted, and R-143 and/or R-1132(E,Z) can be obtained efficiently. Further, when the residence time is set to a value equal to or less than the upper limit of the above range, side reactions are suppressed, and the thermal decomposition of R-32 is promoted, improving the productivity.

The form of the reactor in which the starting material gas is subjected to the reaction is not limited, and known reactors capable of withstanding the reaction temperature and reaction pressure stated above are widely usable. For example, a tubular flow reactor packed with a catalyst may be used. Examples of the catalyst include metal oxide catalysts, such as $Al_2O_3$ and $CoO_2$; metal catalysts, such as Fe, Zn, and Co; and catalysts in which metal particles are supported on oxide or carbon carriers, such as Pd/C and $Pd/TiO_2$. When the reaction is performed in the absence of a catalyst, the reactor may be, for example, a hollow adiabatic reactor, or an adiabatic reactor packed with a porous or non-porous metal or medium that improves the mixing state of the starting material gas. Also usable is a multitubular reactor or the like in which a heat medium is used to cool the reactor and/or to homogenize the temperature distribution within the reactor.

When a hollow reactor is used, in a method wherein a reactor with a smaller inner diameter is used to improve heat transfer efficiency, it is preferable, for example, that the relationship between the flow rate of the starting material gas and the inner diameter of the reactor be adjusted so that a high linear velocity and a large heat transfer area are obtained.

Specifically, the reactor is preferably formed of a material that is resistant to the corrosive action, such as Hastelloy, Inconel, Monel, Incoloy, and stainless steel materials (e.g., SUS316). When a metal reactor with an iron content of 10 mass % or less, such as a reactor of Hastelloy or Inconel, is used from among the reactors above, the occurrence of caulking on the reactor inner wall can also be suppressed.

The reaction gas containing R-143 and/or R-1132(E,Z) obtained in embodiment 2 may be appropriately subjected to a purification step to extract high-purity R-143 and/or R-1132(E,Z). The purification method may be a known purification method, such as distillation. In embodiment 2, although it depends on the reaction conditions, in a preferred embodiment, the selectivity of R-143 is 20 mol % or more (particularly 30 to 60 mol %), the selectivity of R-1132(E) is 2 mol % or more (particularly 2 to 7 mol %), the selectivity of R-1132(Z) is 3 mol % or more (particularly 3 to 11 mol %), and the total selectivity of these is preferably 25 mol % or more (particularly 30 to 70 mol %).

When the reaction gas of embodiment 2 contains R-143, R-143 contained in the reaction gas is used as a new starting material gas, and R-143 is dehydrofluorinated, whereby a reaction gas containing R-1132(E,Z) can be obtained. Although R-1132(E,Z) can be directly synthesized by subjecting a starting material gas containing R-32 to a reaction that involves thermal decomposition (synthesis of R-1132 (E,Z) by reaction between CHF carbenes (CHF·) obtained by dehydrofluorination of R-32), there is a characteristic that the amount of by-products is smaller when R-1132(E,Z) is obtained by once obtaining a reaction gas containing R-143 through embodiment 2, using R-143 as a new starting material gas, and dehydrofluorinating R-143. That is, R-143 contained in the reaction gas of embodiment 2 is useful as a new starting material gas for obtaining R-1132(E,Z) with high selectivity.

Embodiment 3

Embodiment 3 is a method for producing a reaction gas containing R-143 and/or R-1132(E,Z), the method comprising supplying a starting material gas containing difluoromethane (R-32) and a heat medium with a temperature of 600° C. or more and 1000° C. or less in a reactor, and subjecting the starting material gas to a reaction that involves thermal decomposition at a temperature of 600° C. or more and 1000° C. or less, thereby obtaining the reaction gas.

In embodiment 3, a starting material gas containing R-32 and a heat medium with a temperature of 600° C. or more and 1000° C. or less are supplied to a reactor, and the starting material gas is subjected to a reaction that involves thermal decomposition (also simply referred to below as "the reaction") at a temperature of 600° C. or more and 1000° C. or less, whereby a reaction gas containing R-143 and/or R-1132(E,Z), which are the target compounds, can be synthesized. In embodiment 3, at least the heat medium is preheated to a temperature of 600° C. or more and 1000° C. or less before being supplied to the reactor, whereas the starting material gas is not necessarily preheated before being supplied to the reactor. However, the starting material gas may be preheated to a temperature of 600° C. or more and 1000° C. or less together with or separately from the heat medium before being supplied to the reactor. The starting material gas and the heat medium are combined together at any place before each being supplied to the reactor (preferably at the reactor inlet) and then supplied to the reactor.

The operation of preheating the heat medium to a predetermined temperature is performed outside the reactor, the operation of optionally preheating the starting material gas is performed outside the reactor, and the operation of then subjecting the starting material gas to the reaction at a predetermined temperature is performed inside the reactor.

In embodiment 3, R-32 alone may be directly supplied to a reactor as the starting material gas, or R-32 may be supplied after being diluted with an inert gas, such as nitrogen, argon, or carbon dioxide. The content of R-32 in the starting material gas is not limited, but is preferably adjusted in the range of 10 volume % or more and 100 volume % or less, and more preferably 90 volume % or more and 100 volume % or less. By diluting the starting material gas to this range, it is easy to obtain an effect of suppressing a side reaction (caulking) in which R-32 is completely dehydrofluorinated to generate carbon.

The heat medium is a substance that is liquid at room temperature and has a high heat transport capacity and a high heat retention capacity. When a heat medium is used, a predetermined reaction temperature is easily maintained in the reactor efficiently. The heat medium may be any medium that does not directly react with the starting material gas, and examples include water and anhydrous hydrogen fluoride. Such a heat medium may be supplied to the reactor after being heated to a temperature of 600° C. or more and 1000° C. or less under pressure or no pressure outside the reactor. The amount of heat medium used is not limited; however, when the total amount (molar concentration) of the starting material gas and the heat medium during reaction is 100 mol %, the content of the heat medium is preferably 10 to 90 mol %, and more preferably 20 to 70 mol %.

The temperature (reaction temperature) at which the starting material gas is subjected to the reaction in a reactor may be 600° C. or more and 1000° C. or less, and in this range, preferably 700° C. or more and 900° C. or less, and more preferably 800° C. or more and 850° C. or less. When the reaction temperature is set within this range, both the conversion of R-32 and the selectivity of R-143 and/or R-1132(E,Z) can be improved.

The pressure (reaction pressure) at which the starting material gas is subjected to the reaction is preferably 0.1 MPaG or more and 2.0 MPaG or less. In this range, the reaction pressure is more preferably 1.2 MPaG or more and 2.0 MPaG or less, and even more preferably 1.5 MPaG or more and 2.0 MPaG or less. When the pressure is set within this range, both the conversion of R-32 and the selectivity of R-143 and/or R-1132(E,Z) can be improved.

The starting material gas and/or the heat medium (including a case of being a mixed gas thereof) is preferably pre-pressurized to a pressure exceeding the reaction pressure before being supplied to the reactor. The pressure condition of pre-pressurization can be appropriately selected from a pressure range exceeding 0.1 MPaG (e.g., more than 0.1 MPaG and 2.1 MPaG or less). Pre-pressurization can be performed using a known compressor or the like. The lower limit of the pressure condition of pre-pressurization can be set to 0.2 MPaG or more, 0.3 MPaG or more, or the like.

The time (residence time) for which the starting material gas is subjected to the reaction is in accordance with the reaction temperature, reaction pressure, and the like, and cannot be unconditionally determined. However, it is preferably 0.01 seconds or more and 10 seconds or less, and more preferably 0.10 seconds or more and 1 second or less. When the residence time is set to a value equal to or more than the lower limit of the above range, the thermal decomposition of R-32 is promoted, and R-143 can be obtained efficiently. Further, when the residence time is set to a value equal to or less than the upper limit of the above range, side reactions are suppressed, and the thermal decomposition of R-32 is promoted, improving the productivity.

The heating method used when subjecting the starting material gas to the reaction may be a known method. Examples include a method of heating a reactor (reaction container) in an electric furnace, a method of heating a reactor with an electric heater or a jacket through which a heat medium is circulated, a method of heating a reactor in a microwave oven, a method in which the inert gas as a diluent gas is heated and then mixed with R-32, and any combination of these methods.

The time (residence time) for subjecting the starting material gas to the reaction is in accordance with the reaction temperature, reaction pressure, and the like, and cannot be unconditionally determined. However, it is preferably 0.01 seconds or more and 10 seconds or less, and more preferably 0.10 seconds or more and 1 second or less. When the residence time is set to a value equal to or more than the lower limit of the above range, the thermal decomposition of R-32 is promoted, and R-143 and/or R-1132(E,Z) can be obtained efficiently. Further, when the residence time is set to a value equal to or less than the upper limit of the above range, side reactions are suppressed, and the thermal decomposition of R-32 is promoted, improving the productivity.

The form of the reactor in which the starting material gas is subjected to the reaction is not limited, and known reactors capable of withstanding the reaction temperature and reaction pressure stated above are widely usable. For example, a tubular flow reactor packed with a catalyst may be used. Examples of the catalyst include metal oxide catalysts, such as $Al_2O_3$ and $CoO_2$; metal catalysts, such as Fe, Zn, and Co; and catalysts in which metal particles are supported on oxide or carbon carriers, such as Pd/C and $Pd/TiO_2$. When the reaction is performed in the absence of a catalyst, the reactor may be, for example, a hollow adiabatic reactor, or an adiabatic reactor packed with a porous or non-porous metal or medium that improves the mixing state of the starting material gas. Also usable is a multitubular reactor or the like in which a heat medium is used to cool the reactor and/or to homogenize the temperature distribution within the reactor.

When a hollow reactor is used, in a method wherein a reactor with a smaller inner diameter is used to improve heat transfer efficiency, it is preferable, for example, that the relationship between the flow rate of the starting material gas and the inner diameter of the reactor be adjusted so that a high linear velocity and a large heat transfer area are obtained.

Specifically, the reactor is preferably formed of a material that is resistant to the corrosive action, such as Hastelloy, Inconel, Monel, Incoloy, and stainless steel materials (e.g., SUS316). When a metal reactor with an iron content of 10 mass % or less, such as a reactor of Hastelloy or Inconel, is used from among the reactors above, the occurrence of caulking on the reactor inner wall can also be suppressed.

The reaction gas containing R-143 and/or R-1132(E,Z) obtained in embodiment 3 may be appropriately subjected to a purification step to extract high-purity R-143 and/or R-1132 (E,Z). The purification method may be a known purification method, such as distillation. In embodiment 3, although it depends on the reaction conditions, in a preferred embodiment, the selectivity of R-143 is 20 mol % or more (particularly 30 to 60 mol %), the selectivity of R-1132(E) is 2 mol % or more (particularly 2 to 7 mol %), the selectivity of R-1132(Z) is 3 mol % or more (particularly 3 to 11 mol %), and the total selectivity of these is preferably 25 mol % or more (particularly 30 to 70 mol %).

When the reaction gas of embodiment 3 contains R-143, R-143 contained in the reaction gas is used as a new starting material gas, and R-143 is dehydrofluorinated, whereby a reaction gas containing R-1132(E,Z) can be obtained. Although R-1132(E,Z) can be directly synthesized by subjecting a starting material gas containing R-32 to a reaction that involves thermal decomposition (synthesis of R-1132 (E,Z) by reaction between CHF carbenes (CHF·) obtained by dehydrofluorination of R-32), there is a characteristic that the amount of by-products is smaller when R-1132(E,Z) is obtained by once obtaining a reaction gas containing R-143 through embodiment 3, using R-143 as a new starting material gas, and dehydrofluorinating R-143. That is, R-143 contained in the reaction gas of embodiment 3 is useful as a new starting material gas for obtaining R-1132(E,Z) with high selectivity.

Embodiment 4

Embodiment 4 is a method for producing a reaction gas containing R-143 and/or R-1132(E,Z), the method comprising, before supplying a starting material gas containing R-32 in a reactor, combining the starting material gas with a hydrofluorocarbon gas and/or a hydrochlorofluorocarbon gas in an amount of 10% or less of the volume of the R-32 to form a mixed gas, and subjecting the mixed gas to a reaction that involves thermal decomposition at a temperature of 600° C. or more and 1000° C. or less, thereby obtaining the reaction gas.

In embodiment 4, before a starting material gas containing R-32 is supplied to a reactor, the starting material gas is combined with a hydrofluorocarbon gas and/or a hydrochlorofluorocarbon gas (also referred to as "HFC gas etc.") in an amount of 10% or less of the volume of R-32 to form a mixed gas, and the mixed gas is subjected to a reaction that involves thermal decomposition (also simply referred to below as "the reaction") at a temperature of 600° C. or more and 1000° C. or less, whereby a reaction gas containing R-143 and/or R-1132(E,Z), which are the target compounds, can be synthesized. The operation of combining the starting material gas with HFC gas etc. is preferably performed at the reactor inlet, and the operation of then subjecting the mixed gas to the reaction at a predetermined temperature is performed inside the reactor. If necessary, the starting material gas can be preheated together with or separately from HFC gas etc.

In embodiment 4, R-32 alone may be directly supplied to a reactor as the starting material gas, or R-32 may be supplied after being diluted with an inert gas, such as nitrogen, argon, or carbon dioxide. The content of R-32 in the starting material gas is not limited, but is preferably adjusted in the range of 10 volume % or more and 100 volume % or less, and more preferably 90 volume % or more and 100 volume % or less. By diluting the starting material gas to this range, it is easy to obtain an effect of suppressing a side reaction (caulking) in which R-32 is completely dehydrofluorinated to generate carbon.

The starting material gas is preferably combined with HFC gas etc. in an amount of 10% or less of the volume of R-32 at the reactor inlet to form a mixed gas, and then the mixed gas is subjected to a reaction that involves thermal decomposition. The HFC gas etc. may be a hydrofluorocarbon gas and/or a hydrochlorofluorocarbon gas. Specific examples include R-134, R-134a, R-31, R-125, R-143a, R-143, R-23, R-41, R1123, and the like, which are used singly or as a mixed gas of two or more. The HFC gas etc. may be newly mixed with the starting material gas, or those generated as by-products when embodiment 4 is repeatedly performed may be recycled and mixed. By mixing the HFC gas etc., the thermal decomposition rate of R-32 is improved, and high conversion at the same temperature for the same residence time during reaction is easily obtained as compared with R-32 alone. The mixing ratio of the HFC gas etc. may be 10% or less of the volume of R-32, and in this range, preferably 5 volume % or less. The lower limit of the mixing ratio of the HFC gas etc. is not limited, but is preferably 0.01% or more of the volume of R-32.

The temperature (reaction temperature) at which the starting material gas and the HFC gas etc. are combined, and the mixed gas is subjected to the reaction in a reactor may be 600° C. or more and 1000° C. or less, and in this range, preferably 700° C. or more and 900° C. or less, and more preferably 800° C. or more and 850° C. or less. When the reaction temperature is set within this range, both the conversion of R-32 and HFC gas etc. contained in the mixed gas and the selectivity of R-143 and/or R-1132(E,Z) can be improved.

The pressure (reaction pressure) at which the mixed gas is subjected to the reaction is preferably 0.1 MPaG or more and 2.0 MPaG or less. In this range, the reaction pressure is more preferably 1.2 MPaG or more and 2.0 MPaG or less, and even more preferably 1.5 MPaG or more and 2.0 MPaG or less. When the pressure is set within this range, both the conversion of R-32 and HFC gas etc. contained in the mixed gas and the selectivity of R-143 and/or R-1132(E,Z) can be improved.

The starting material gas and/or the HFC gas etc. (including a case of being a mixed gas thereof) is preferably pre-pressurized to a pressure exceeding the reaction pressure before being supplied to the reactor. The pressure condition of pre-pressurization can be appropriately selected from a pressure range exceeding 0.1 MPaG (e.g., more than 0.1 MPaG and 2.1 MPaG or less). Pre-pressurization can be performed using a known compressor or the like. The lower limit of the pressure condition of pre-pressurization can be set to 0.2 MPaG or more, 0.3 MPaG or more, or the like.

The heating method used when subjecting the mixed gas to the reaction may be a known method. Examples include a method of heating a reactor (reaction container) in an electric furnace, a method of heating a reactor with an electric heater or a jacket through which a heat medium is circulated, a method of heating a reactor in a microwave oven, a method in which the inert gas as a diluent gas is heated and then mixed with R-32, and any combination of these methods.

The time (residence time) for subjecting the mixed gas to the reaction is in accordance with the reaction temperature, reaction pressure, and the like, and cannot be unconditionally determined. However, it is preferably 0.01 seconds or more and 10 seconds or less, and more preferably 0.10 seconds or more and 1 second or less. When the residence time is set to a value equal to or more than the lower limit of the above range, the thermal decomposition of R-32 is promoted, and R-143 and/or R-1132(E,Z) can be obtained efficiently. Further, when the residence time is set to a value equal to or less than the upper limit of the above range, side reactions are suppressed, and the thermal decomposition of R-32 is promoted, improving the productivity.

The form of the reactor in which the mixed gas is subjected to the reaction is not limited, and known reactors capable of withstanding the reaction temperature and reaction pressure stated above are widely usable. For example, a tubular flow reactor packed with a catalyst may be used. Examples of the catalyst include metal oxide catalysts, such as $Al_2O_3$ and $CoO_2$; metal catalysts, such as Fe, Zn, and Co; and catalysts in which metal particles are supported on oxide or carbon carriers, such as Pd/C and $Pd/TiO_2$. When the reaction is performed in the absence of a catalyst, the reactor may be, for example, a hollow adiabatic reactor, or an adiabatic reactor packed with a porous or non-porous metal or medium that improves the mixing state of the mixed gas. Also usable is a multitubular reactor or the like in which a heat medium is used to cool the reactor and/or to homogenize the temperature distribution within the reactor.

When a hollow reactor is used, in a method wherein a reactor with a smaller inner diameter is used to improve heat transfer efficiency, it is preferable, for example, that the relationship between the flow rate of the starting material gas and the inner diameter of the reactor be adjusted so that a high linear velocity and a large heat transfer area are obtained.

Specifically, the reactor is preferably formed of a material that is resistant to the corrosive action, such as Hastelloy, Inconel, Monel, Incoloy, and stainless steel materials (e.g., SUS316). When a metal reactor with an iron content of 10 mass % or less, such as a reactor of Hastelloy or Inconel, is used from among the reactors above, the occurrence of caulking on the reactor inner wall can also be suppressed.

The reaction gas containing R-143 and/or R-1132(E,Z) obtained in embodiment 4 may be appropriately subjected to a purification step to extract high-purity R-143 and/or R-1132 (E,Z). The purification method may be a known purification method, such as distillation. In embodiment 4, although it depends on the reaction conditions, in a preferred embodiment, the selectivity of R-143 is 20 mol % or more (particularly 30 to 60 mol %), the selectivity of R-1132(E) is 2 mol % or more (particularly 2 to 7 mol %), the selectivity of R-1132(Z) is 3 mol % or more (particularly 3 to 11 mol %), and the total selectivity of these is preferably 25 mol % or more (particularly 30 to 70 mol %).

When the reaction gas of embodiment 4 contains R-143, R-143 contained in the reaction gas is used as a new starting material gas, and R-143 is dehydrofluorinated, whereby a reaction gas containing R-1132(E,Z) can be obtained. Although R-1132(E,Z) can be directly synthesized by subjecting a starting material gas containing R-32 to a reaction that involves thermal decomposition (synthesis of R-1132 (E,Z) by reaction between CHF carbenes (CHF·) obtained by dehydrofluorination of R-32), there is a characteristic that the amount of by-products is smaller when R-1132(E,Z) is obtained by once obtaining a reaction gas containing R-143 through embodiment 4, using R-143 as a new starting material gas, and dehydrofluorinating R-143. That is, R-143 contained in the reaction gas of embodiment 4 is useful as a new starting material gas for obtaining R-1132 (E,Z) with high selectivity.

The embodiments of the present disclosure are described as above. However, the present disclosure is not limited to these embodiments, and can include various embodiments as long as they do not deviate from the gist of the disclosure.

As described above, the present disclosure includes the subject matter described in the following items.

1. A method for producing a reaction gas containing 1,1,2-trifluoroethane (R-143) and/or (E,Z)-1,2-difluoroethylene (R-1132(E,Z)), the method comprising subjecting a starting material gas containing difluoromethane (R-32) to a reaction that involves thermal decomposition at a pressure of 0.6 MPaG or more and 2.0 MPaG or less and a temperature of 600° C. or more and 1000° C. or less, thereby obtaining the reaction gas.
2. A method for producing a reaction gas containing 1,1,2-trifluoroethane (R-143) and/or (E,Z)-1,2-difluoroethylene (R-1132(E,Z)), the method comprising supplying a starting material gas containing difluoromethane (R-32), which has been pre-pressurized to a pressure of 0.1 MPaG or more and 2.0 MPaG or less, in a reactor under a pressure condition lower than the pre-pressurization pressure, and subjecting the starting material gas to a reaction that involves thermal decomposition at a temperature of 600° C. or more and 1000° C. or less, thereby obtaining the reaction gas.
3. A method for producing a reaction gas containing 1,1,2-trifluoroethane (R-143) and/or (E,Z)-1,2-difluoroethylene (R-1132(E,Z)), the method comprising supplying a starting material gas containing difluoromethane (R-32) and a heat medium with a temperature of 600° C. or more and 1000° C. or less in a reactor, and subjecting the starting material gas to a reaction that involves thermal decomposition at a temperature of 600° C. or more and 1000° C. or less, thereby obtaining the reaction gas.
4. A method for producing a reaction gas containing 1,1,2-trifluoroethane (R-143) and/or (E,Z)-1,2-difluoroethylene (R-1132(E,Z)), the method comprising, before supplying a starting material gas containing difluoromethane (R-32) in a reactor, combining the starting material gas with a hydrofluorocarbon gas and/or a hydrochlorofluorocarbon gas in an amount of 10% or less of the volume of the difluoromethane (R-32) to form a mixed gas, and subjecting the mixed gas to a reaction that involves thermal decomposition at a temperature of 600° C. or more and 1000° C. or less, thereby obtaining the reaction gas.
5. The production method according to any one of Items 2 to 4, wherein the reaction is performed at a pressure in the range of 0 MPaG or more and less than 2.0 MPaG.
6. The production method according to any one of Items 1 to 5, wherein the reaction is performed by using a metal reactor with an iron content of 10 mass % or less.
7. The production method according to any one of Items 1 to 6, wherein the starting material gas contains the difluoromethane (R-32) in an amount of 10 volume % or more and 100 volume % or less.
8. The production method according to any one of Items 1 to 7, wherein the reaction is performed at a temperature of 700° C. or more and 900° C. or less.
9. The production method according to any one of Items 1 to 8, wherein the time (residence time) for subjecting the starting material gas to the reaction is in the range of 0.01 seconds or more and 10 seconds or less.
10. A method for producing (E,Z)-1,2-difluoroethylene (R-1132(E,Z)), wherein in the production method according to any one of Items 1 to 9, the reaction gas contains 1,1,2-trifluoroethane (R-143), and the method comprises subjecting 1,1,2-trifluoroethane (R-143) contained in the reaction gas to a dehydrofluorination reaction.

EXAMPLES

Embodiments 1 to 4 of the production methods of the present disclosure are described in more detail below based on experimental examples. However, the production methods of the present disclosure are not limited to the scope of the experimental examples.

In Experimental Examples 1 to 4 below, the composition of each component was analyzed by gas chromatography (MS detector).

Experimental Example 1 (Embodiment 2: Effect of Pressurization Conditions on Reaction Results)

Under the reaction conditions shown in Table 1, a starting material gas containing R-32 alone was subjected to a reaction involving thermal decomposition, thereby obtaining a reaction gas containing R-143 and R-1132(E,Z).

TABLE 1

| | No. 1 | No. 2 | No. 3 | No. 4 |
|---|---|---|---|---|
| Reaction conditions | | | | |
| Starting material gas | R32 | R32 | R32 | R32 |
| Reaction tube material | Inconel 600 | Inconel 600 | Inconel 600 | Inconel 600 |
| Pre-pressurization pressure (MPaG) | 0.35 | 0.98 | 0.66 | 1.5 |
| Reaction pressure (MPaG) | 0.3 | 0.9 | 0.6 | 1.4 |
| Reaction temperature (° C.) | 850 | 850 | 850 | 850 |
| Residence time (sec) | 0.17 | 0.17 | 0.17 | 0.17 |
| Reaction results | | | | |
| Starting material conversion | 3.3% | 4.4% | 3.9% | 5.0% |
| Yield of R143 and R1132(E, Z) (%) | 1.8% | 2.6% | 2.2% | 3.1% |
| Selectivity in reaction gas | | | | |
| CH4 | 0.5% | 0.4% | 0.4% | 0.3% |
| R23 | 2.3% | 1.9% | 2.0% | 1.6% |
| VDF | 2.5% | 2.1% | 2.2% | 1.9% |
| CH≡CH | 1.1% | 0.9% | 0.9% | 0.8% |
| R1123 | 1.4% | 0.9% | 1.1% | 0.7% |
| R41 | 10.6% | 9.8% | 10.1% | 9.4% |
| R1132E | 6.7% | 3.6% | 5.0% | 2.1% |
| R143a | 0.0% | 0.0% | 0.0% | 0.0% |
| R1132Z | 10.9% | 5.9% | 8.1% | 3.3% |
| R134a | 6.5% | 5.1% | 5.6% | 4.6% |

TABLE 1-continued

| | No. 1 | No. 2 | No. 3 | No. 4 |
|---|---|---|---|---|
| R134 | 20.1% | 19.3% | 19.7% | 18.7% |
| R143 | 35.6% | 48.9% | 43.3% | 55.6% |
| Others | 1.8% | 1.2% | 1.5% | 1.0% |

As is clear from the results of Table 1, it is revealed that target products (R-143, R-1132(E), and R-1132(Z)) can be obtained with high selectivity (total selectivity of these products) by the production method of embodiment 2 using a starting material that is easier to obtain than those used in conventional methods.

Experimental Example 2 (Embodiment 3: Effect of Presence or Absence of Heat Medium on Reaction Results)

Under the reaction conditions shown in Table 2, a starting material gas containing R-32 alone was subjected to a reaction involving thermal decomposition using a heat medium, thereby obtaining a reaction gas containing R-143 and R-1132 (E,Z).

TABLE 2

| | No. 1 | No. 2 |
|---|---|---|
| Reaction conditions | | |
| Starting material gas | R32 | R32 |
| Reaction tube material | Inconel 600 | Inconel 600 |
| Pre-pressurization pressure (MPaG) | 0.22 | 0.22 |
| Reaction pressure (MPaG) | 0.2 | 0.2 |
| Reaction temperature (° C.) | 800 | 800 |
| Residence time (sec) | 1.83 | 1.83 |
| Dilution gas | None | HF |
| Molar concentration of heat medium (%) | — | 60 |
| Reaction results | | |
| Conversion | 6.2% | 7.9% |
| Total yield of R143 + R1132(E, Z) (%) | 2.9% | 3.9% |
| Selectivity in reaction gas | | |
| CH4 | 0.4% | 0.5% |
| R23 | 1.9% | 2.1% |
| VDF | 3.3% | 2.6% |
| CH≡CH | 1.3% | 0.1% |
| R1123 | 1.4% | 1.4% |
| R41 | 12.9% | 12.3% |
| R1132E | 6.7% | 4.7% |
| R143a | 0.0% | 0.0% |
| R1132Z | 11.2% | 6.6% |
| R134a | 5.3% | 5.0% |
| R134 | 25.7% | 24.1% |
| R143 | 28.6% | 37.6% |
| Others | 1.2% | 3.0% |

As is clear from the results of Table 2, it is revealed that target products (R-143, R-1132(E), and R-1132(Z)) can be obtained with high selectivity (total selectivity of these products) by the production method of embodiment 3 using a starting material that is easier to obtain than those used in conventional methods.

Experimental Example 3 (Embodiment 4: Effect of Presence or Absence of Additive Gas on Reaction Results)

Under the reaction conditions shown in Table 3, a starting material gas containing R-32 alone was mixed with an additive gas, and the resulting mixed gas was subjected to a reaction involving thermal decomposition, thereby obtaining a reaction gas containing R-143 and R-1132(E,Z).

TABLE 3

| | No. 1 | No. 2 |
|---|---|---|
| Reaction conditions | | |
| Starting material gas | R32 | R32 |
| Type of additive gas | R31 | None |
| Reaction tube material | SUS316 | SUS316 |
| Pre-pressurization pressure (MPaG) | 0.007 | 0.007 |
| Reaction pressure (MPaG) | 0.005 | 0.005 |
| Temperature (° C.) | 900 | 900 |
| Residence time (sec) | 0.1 | 0.1 |
| Additive gas volume % | 1 | 0 |
| Reaction results | | |
| Starting material conversion | 7.1% | 5.6% |
| Total yield of R143 + R1132(E, Z) (%) | 3.3% | 1.1% |
| Selectivity in reaction gas | | |
| CH4 | 0.0% | 0.4% |
| CH≡CH | 0.5% | 1.4% |
| CO2 | 0.0% | 0.0% |
| R23 | 0.0% | 1.2% |
| VDF | 0.0% | 2.8% |
| R1123 | 3.0% | 3.7% |
| R41 | 10.0% | 16.5% |
| R1132E | 18.0% | 7.3% |
| R1132Z | 28.0% | 11.2% |
| R134 | 2.0% | 15.0% |
| R143 | 21.5% | 10.6% |
| R143a | 1.0% | 2.0% |
| Others | 16.0% | 27.9% |

As is clear from the results of Table 3, it is revealed that target products (R-143, R-1132(E), and R-1132(Z)) can be obtained with high selectivity (total selectivity of these products) by the production method of embodiment 4 using a starting material that is easier to obtain than those used in conventional methods.

Experimental Example 4 (Effect of Difference in Starting Material Gas on Reaction Results)

Under the reaction conditions shown in Table 4, R-32 and R143 were each used as a starting material gas, thereby obtaining a reaction gas containing R-1132(E,Z).

TABLE 4

| Reaction conditions | Production of R1132 directly from R32 | Production of R1132 from R143 using HF removal catalyst |
|---|---|---|
| Starting material gas | R32 | R143 |
| Reaction tube material | Inconel 600 | Inconel 600 |
| Pre-pressurization pressure (MPaG) | 0.35 | 0.35 |
| Reaction pressure (MPaG) | 0.3 | 0.3 |
| Reaction temperature (° C.) | 850 | 850 |
| Residence time (sec) | 0.17 | 0.17 |
| Reaction results | | |
| Starting material conversion | 3.3% | 3.3% |
| R1132(E, Z) selectivity (%) | 18% | 52.3% |
| Selectivity in reaction gas | | |
| CH4 | 0.5% | 0.5% |
| R23 | 2.3% | 2.3% |
| VDF | 2.5% | 2.5% |
| CH≡CH | 1.1% | 1.1% |
| R1123 | 1.4% | 1.4% |

TABLE 4-continued

| Reaction conditions | Production of R1132 directly from R32 | Production of R1132 from R143 using HF removal catalyst |
|---|---|---|
| R41 | 10.6% | 10.6% |
| R1132E | 6.7% | 11.2% |
| R143a | 0.0% | 0.1% |
| R1132Z | 10.9% | 41.1% |
| R134a | 6.5% | 6.5% |
| R134 | 20.1% | 20.1% |
| R143 | 35.6% | 0.0% |
| Others | 1.8% | 2.5% |

As is clear from the results of Table 4, it is revealed that compared with when using R-32 as a starting material gas to obtain a reaction gas containing R-1132(E,Z), when using R-143 as a starting material gas to obtain a reaction gas containing R-1132(E,Z), the selectivity of the target product was higher (fewer by-products).

Experimental Example 5 (Effect of Difference in Reaction Pressure on Reaction Results)

A starting material gas containing R-32 alone was subjected to a reaction involving thermal decomposition, thereby obtaining a reaction gas containing R-143 and R-1132 (E,Z). As the reaction conditions, the residence time was adjusted to so that R-32 conversion was 5 mol %, and the reaction temperature was fixed at 800° C. The FIGURE shows the effect of difference in reaction pressure on the reaction results.

As is clear from the results of the FIGURE, it is revealed that in order to obtain the target products (R-143, R-1132 (E), and R-1132 (Z)) with high selectivity (total selectivity of these products), the reaction pressure is preferably 0.5 MPaG or more and 2.0 MPa or less, more preferably 1.0 MPaG or more and 2.0 MPa or less, and even more preferably 1.5 MPaG or more and 2.0 MPa or less.

The invention claimed is:

1. A method for producing a reaction gas containing 1,1,2-trifluoroethane (R-143) and (E,Z)-1,2-difluoroethylene (R-1132 (E,Z)), the method comprising subjecting a starting material gas containing difluoromethane (R-32) to a reaction that involves thermal decomposition at a pressure of 0.9 MPaG or more and 2.0 MPaG or less and a temperature of 600° C. or more and 1000° C. or less, thereby obtaining the reaction gas, wherein the selectivity of R-143 in the reaction gas is 30 to 60 mol %.

2. A method for producing a reaction gas containing 1,1,2-trifluoroethane (R-143) and (E,Z)-1,2-difluoroethylene (R-1132 (E,Z)), the method comprising supplying a starting material gas containing difluoromethane (R-32), which has been pre-pressurized to a pressure of 0.1 MPaG or more and 2.0 MPaG or less, in a reactor under a pressure condition lower than the pre-pressurization pressure, and subjecting the starting material gas to a reaction that involves thermal decomposition at a temperature of 600° C. or more and 1000° C. or less, thereby obtaining the reaction gas, wherein the selectivity of R-143 in the reaction gas is 30 to 60 mol %.

3. A method for producing a reaction gas containing 1,1,2-trifluoroethane (R-143) and/or (E,Z)-1,2-difluoroethylene (R-1132 (E,Z)), the method comprising supplying a starting material gas containing difluoromethane (R-32) and a heat medium with a temperature of 600° C. or more and 1000° C. or less in a reactor, and subjecting the starting material gas to a reaction that involves thermal decomposition at a temperature of 600° C. or more and 1000° C. or less, thereby obtaining the reaction gas, wherein the heat medium contains anhydrous hydrogen fluoride.

4. A method for producing a reaction gas containing 1,1,2-trifluoroethane (R-143) and/or (E,Z)-1,2-difluoroethylene (R-1132 (E,Z)), the method comprising, before supplying a starting material gas containing difluoromethane (R-32) in a reactor, combining the starting material gas with chlorofluoromethane (R-31) in an amount of 0.01% or more and 10% or less of the volume of the difluoromethane (R-32) to form a mixed gas, and subjecting the mixed gas to a reaction that involves thermal decomposition at a temperature of 600° C. or more and 1000° C. or less, thereby obtaining the reaction gas.

5. The production method according to claim 1, wherein the reaction is performed by using a metal reactor with an iron content of 10 mass % or less.

6. The production method according to claim 1, wherein the starting material gas contains the difluoromethane (R-32) in an amount of 10 volume % or more and 100 volume % or less.

7. The production method according to claim 1, wherein the reaction is performed at a temperature of 700° C. or more and 900° C. or less.

8. The production method according to claim 1, wherein a residence time for subjecting the starting material gas to the reaction is in the range of 0.01 seconds or more and 10 seconds or less.

9. A method for producing (E,Z)-1,2-difluoroethylene (R-1132 (E,Z)), wherein in the production method according to claim 1, the reaction gas contains 1,1,2-trifluoroethane (R-143), and the method comprises subjecting 1,1,2-trifluoroethane (R-143) contained in the reaction gas to a dehydrofluorination reaction.

10. The production method according to claim 2, wherein the reaction is performed at a pressure in the range of 0 MPaG or more and less than 2.0 MPaG.

* * * * *